United States Patent [19]

Commarmot et al.

[11] Patent Number: 4,693,867
[45] Date of Patent: Sep. 15, 1987

[54] MINERALIZATION APPARATUS FOR THE INDIVIDUAL, AUTOMATIC, TREATMENT OF SAMPLES OF PRODUCTS PLACED IN RECIPIENTS

[75] Inventors: Roger Commarmot, Lyons; Dominique Didenot, Meyzieu; Jean-Francois Gardais, Chuzelles, all of France

[73] Assignee: Societe Prolabo (Societe Anonyme), France

[21] Appl. No.: 706,338

[22] Filed: Feb. 27, 1985

[30] Foreign Application Priority Data

Mar. 5, 1984 [FR] France ................... 84 03571

[51] Int. Cl.⁴ .............. G01N 31/12; H05B 6/64
[52] U.S. Cl. ................ 422/64; 219/10.55 R; 422/65; 422/78; 422/102
[58] Field of Search .................. 422/63–68, 422/102, 99; 219/10.55 R, 10.55 D, 10.55 A; 34/1

[56] References Cited

U.S. PATENT DOCUMENTS

| 3,466,146 | 9/1969 | Tabourin . | |
| 3,467,500 | 9/1969 | Wilkinson et al. . | |
| 3,504,376 | 3/1970 | Bednar et al. | 422/64 |
| 3,684,452 | 8/1972 | Bessman | 422/64 |
| 3,694,157 | 9/1972 | Koch et al. | 422/78 |
| 3,745,292 | 7/1973 | Couasnard | 219/10.55 |
| 3,826,622 | 7/1974 | Natelson | 422/65 |
| 3,973,910 | 8/1976 | Fine | 436/172 |
| 4,080,168 | 3/1978 | Samra et al. . | |
| 4,091,323 | 5/1978 | Landis | 422/64 |
| 4,113,436 | 9/1978 | Werder et al. | 422/65 |
| 4,242,301 | 12/1980 | Heyenman et al. | 422/68 |
| 4,347,216 | 8/1982 | Kawasaki et al. | 422/78 |
| 4,391,774 | 7/1983 | DuPain | 422/63 |
| 4,456,580 | 6/1984 | Yamada et al. | 422/65 |
| 4,528,159 | 7/1985 | Liston | 422/65 |

FOREIGN PATENT DOCUMENTS 59-17159  1/1984  Japan ...................... 422/64

OTHER PUBLICATIONS

Patents Abstracts of Japan, vol. 2, No. 1, Jan. 5, 1978, p. 9416 E 77.

Primary Examiner—Michael Marcus
Attorney, Agent, or Firm—Bacon & Thomas

[57] ABSTRACT

The present invention relates to an apparatus for the mineralization of compounds which includes a micro-wave heating chamber which receives the sample containing portion of a sample container and has a stack which surrounds the upper portion of the sample container which extends out of the micro-wave heating chamber. The apparatus further includes a transporting system which supplies the sample containers to the micro-wave heating chamber in individual, automatic and random succession.

15 Claims, 15 Drawing Figures

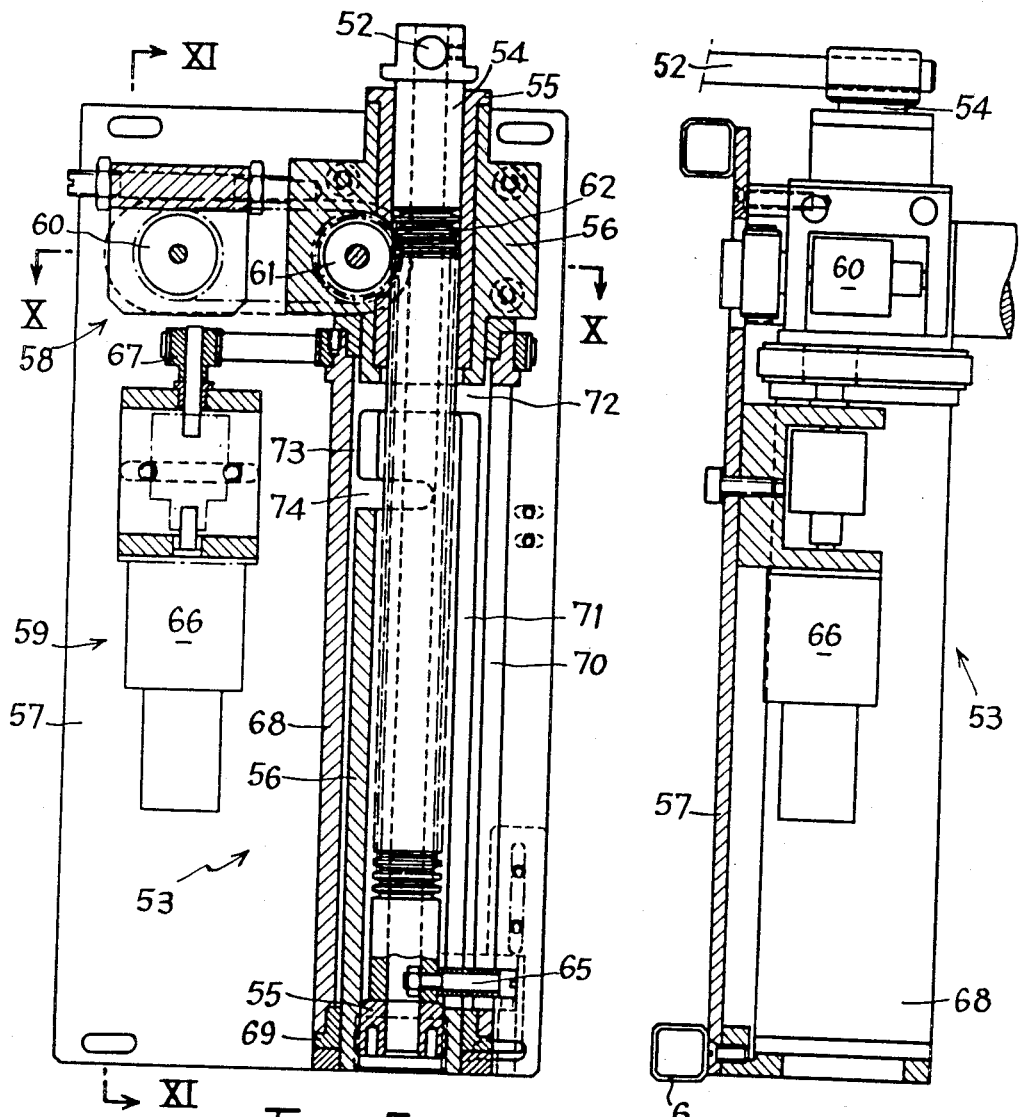
Fig-9
Fig-11
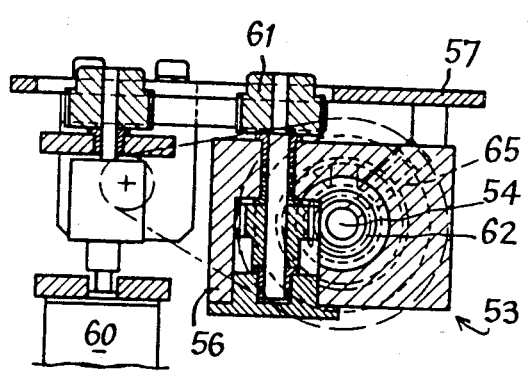
Fig-10

MINERALIZATION APPARATUS FOR THE INDIVIDUAL, AUTOMATIC, TREATMENT OF SAMPLES OF PRODUCTS PLACED IN RECIPIENTS

The present invention relates to the technical domain of mineralization, also called digestion, of inorganic, organic or organometallic compounds.

It is known that it is necessary, before the majority of compound analysis treatments to proceed with a mineralization by wet process by means of concentrated acids, such as sulfuric acid, nitric acid, perchloric acid, or mixtures of these acids.

In order to carry out such a prior analysis treatment, a conventional method consists of disposing in a container, for example of the flask type, a dose of compound to be analyzed, as well as the necessary complementary volume of specific concentrated reagent.

The container is then heated and permanently watched by an operator whose job is to regulate periodically the calories transmitted to the container in order to avoid foaming and overflow of the product. The operator must also periodically but frequently stir the mixture subjected to heating, in order to maintain a good homogeneity of the dissolved and heated compound.

Such operator attention is long, fastidious and likely to lead to physical accidents, sometimes serious for the operator, by the risks of explosion, projections of the composition and by the emanation of corrosive fumes.

In addition to the drawbacks mentioned above, it should be noted that the method thus applied does not make it possible to monitor effectively the possible departure of fractions of the products included in the basis composition and entrained by the fumes and vapours which escape from the neck of the container. It follows that the subsequent result of analysis is considerably disturbed without a means of control for assessing the existence and importance of this random negative factor.

In an attempt to perfect such a process, different propositions of improvement have been developed and carried out.

For example, installations have been proposed which employ, as heating means, instead of a direct flame, a bank of crucibles with infra-red radiation of which the power of each may be regulated by acting on an individual electrical supply. Such a bank of crucibles is associated with a fume collector common to all the crucibles and connected to a pumping unit.

Although such modifications have brought a certain improvement, they do not solve the problems of permanent surveillance, stirring and uncertainty of the results obtained, as these three factors are always a function of the permanent attention of one or more operators.

Furthermore, the operation of such an installation requires a particularly delicate know-how. In fact, regulation of the heating power of each crucible must be assessed as a function of the thermal inertia of such an apparatus and consequently requires considerable experience to assess the anticipation factor to be retained for the increase, but also for the reduction, in the temperature imposed on a sample.

Still with a view to improving such a process for prior analysis treatment, it has been proposed to use, as heat generator, a micro-wave oven provided with a fume and vapour suction port.

U.S. Pat. No. 4,080,168 teaches such a proposition and recommends the use of a micro-wave oven in the cavity of which is placed a flask containing the sample to be treated.

This technique presents certain advantages, as the application of micro-waves allows a quasi-uniform distribution of the energy and therefore a thorough heating of the compound to be treated. For the same reasons, such a technique makes it possible to break the foams which ordinarily develop when the temperature of the compound rises. A permanent surveillance of the development of the treatment is therefore no longer necessary and thus relieves an operator of this fastidious and dangerous aspect of the prior known method.

In addition, a mirco-wave oven is known for its lack of thermal inertia, which makes it possible to regulate more precisely the energy imposed on the sample.

Such a proposition therefore brings a certain improvement to the prior known method but does not solve the general problem of mineralization or digestion encountered in practice in the industry.

In fact, the carrying out of a process of manufacturing or of production in the general sense of various products, such as chemical, pharmaceutical, food products, involves, in order to know for certain the composition and subsequent properties of such a product, periodic, and often frequent, monitoring both the basic compounds and the intermediate products, as well, of course, as the final product, in order to be able to adjust, with a short response time, the parameters for carrying out the process. Fine regulation makes it possible to obtain a final product responding exactly to the specification on its manufacture by presenting variations of composition or of properties within a range of admitted tolerances.

In the contrary case, a process of manufacture which is badly carried out furnishes a large quantity of product which must be discarded or downgraded.

In the industrial field, it would therefore be desirable to be able to have means for treating, automatically but individually, samples of different products arriving at random, i.e. without predetermined order which have to be subjected to a specific treatment by reason of their nature or of the desired result. Such means would in fact make it possible to obtain, rapidly and surely, precise results of analysis which may be used immediately for controlling, modulating or regulating intermediate phases of a process for manufacturing a product.

It will be readily understood that such a need is not satisfied by the known technique, as the manual method is long, dangerous, uncertain. The technique according to U.S. Pat. No. 4,080,168 does not bring a solution to this problem, as it appears obvious that, due to the risk of cross-pollution, such a micro-wave oven cannot be used for subjecting several samples to a treatment of mineralization, for example samples of various natures or having to be subjected to a different treatment. The overall operating conditions of such an oven in fact make it impossible to obtain the result that should be attained in order to satisfy the need of the present industry for carrying out the processes of manufacture or obtaining various products and in the supply of final products having, in time, particular or overall characteristics which are stable, precise and constant.

It is precisely an object of the present invention to bring a solution to the problem thus raised and, to this end, it proposes a novel apparatus for mineralization or digestion making it possible to carry out the individual, but automatic, treatment of samples of products or compounds placed in marked containers and having to be subjected, individually, to treatments which differ by the method, duration and/or temperature imposed thereon.

One object of the invention is to provide a mineralization apparatus which may be placed within the limits of a plurality of lines of sampling of products at different stages of one or more processes for manufacturing or obtaining one or more final products, so as to be able to treat the samples arriving at random, automatically but whilst applying an individual treatment.

The apparatus according to the present invention responds positively to such an objective and thus makes it possible to furnish, upstream of an analysis chain, the characteristic pre-treatments specific to each sample, with a view to making the necesary corrections to these operational parameters, if need be and with a short response time.

To attain the purposes set forth hereinabove, the mineralization apparatus according to the invention is characterized in that it comprises:

- a micro-wave heating chamber adapted to receive solely the sample containing portion of sample container means having an enlarged sample containing portion at a lower end thereof and an upwardly extending neck portion capable of being placed in and removed from the chamber through an opening in an upper wall thereof and bordered by a stack adapted to surround the neck portion of the sample container,
- a device for conducting to a fixed station sample container means placed in individual housings, in random succession and of individual presentation,
- means for detecting at least one characteristic of treatment specific to each sample of product brought and presented to the fixed station by a sample container means,
- a means for individual transfer between the device and the micro-wave heating chamber, and vice versa, of a sample container means presented to the fixed station,
- and a unit for controlling the automatic operation of the apparatus in a cycle specific to each sample to be treated and to which are connected at least the means of detecting at least one characteristic of treatment of each sample.

The invention will be more readily understood on reading the following description with reference to the accompanying drawings, in which:

FIG. 9 is a sectional elevation taken, on a larger scale, along plane IX—IX of FIG. 2.

FIGS. 10 and 11 are sections taken, respectively, along lines X—X of XI—XI of FIG. 9.

Figure 1:
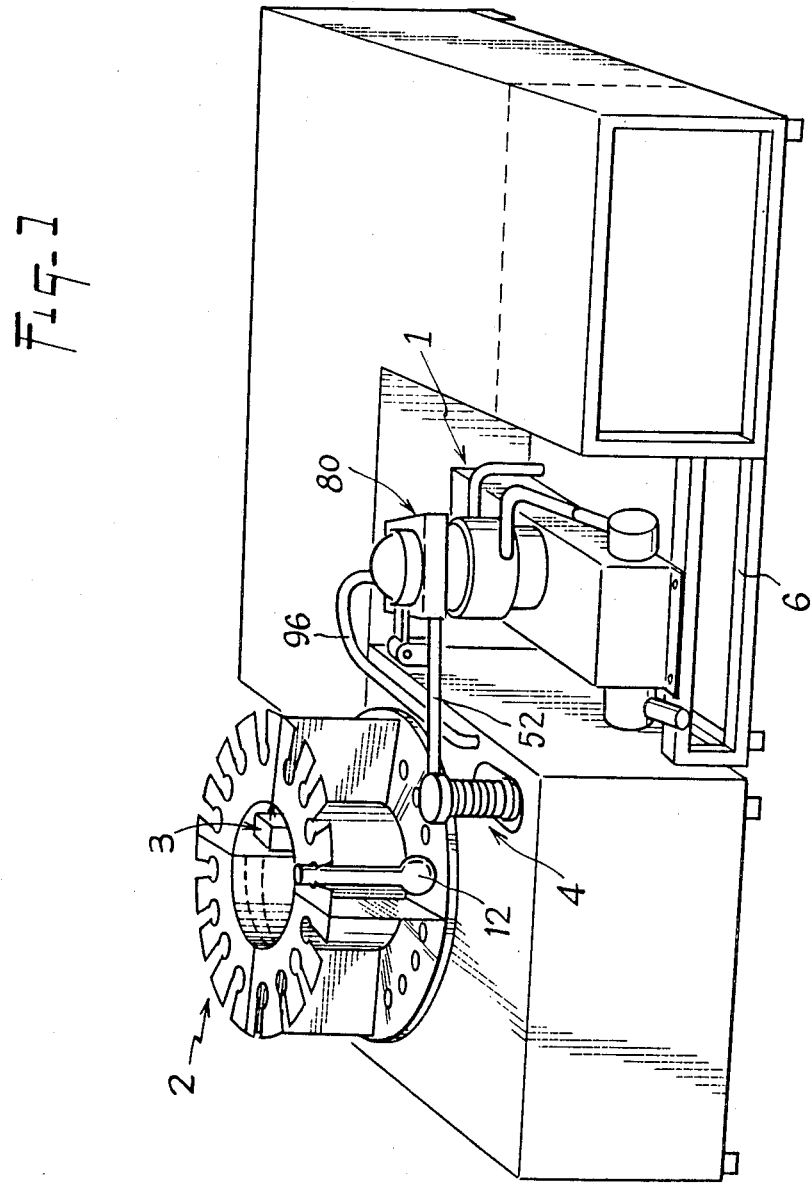
FIG. 1 is a perspective view of an apparatus according to the invention.
Figure 2:
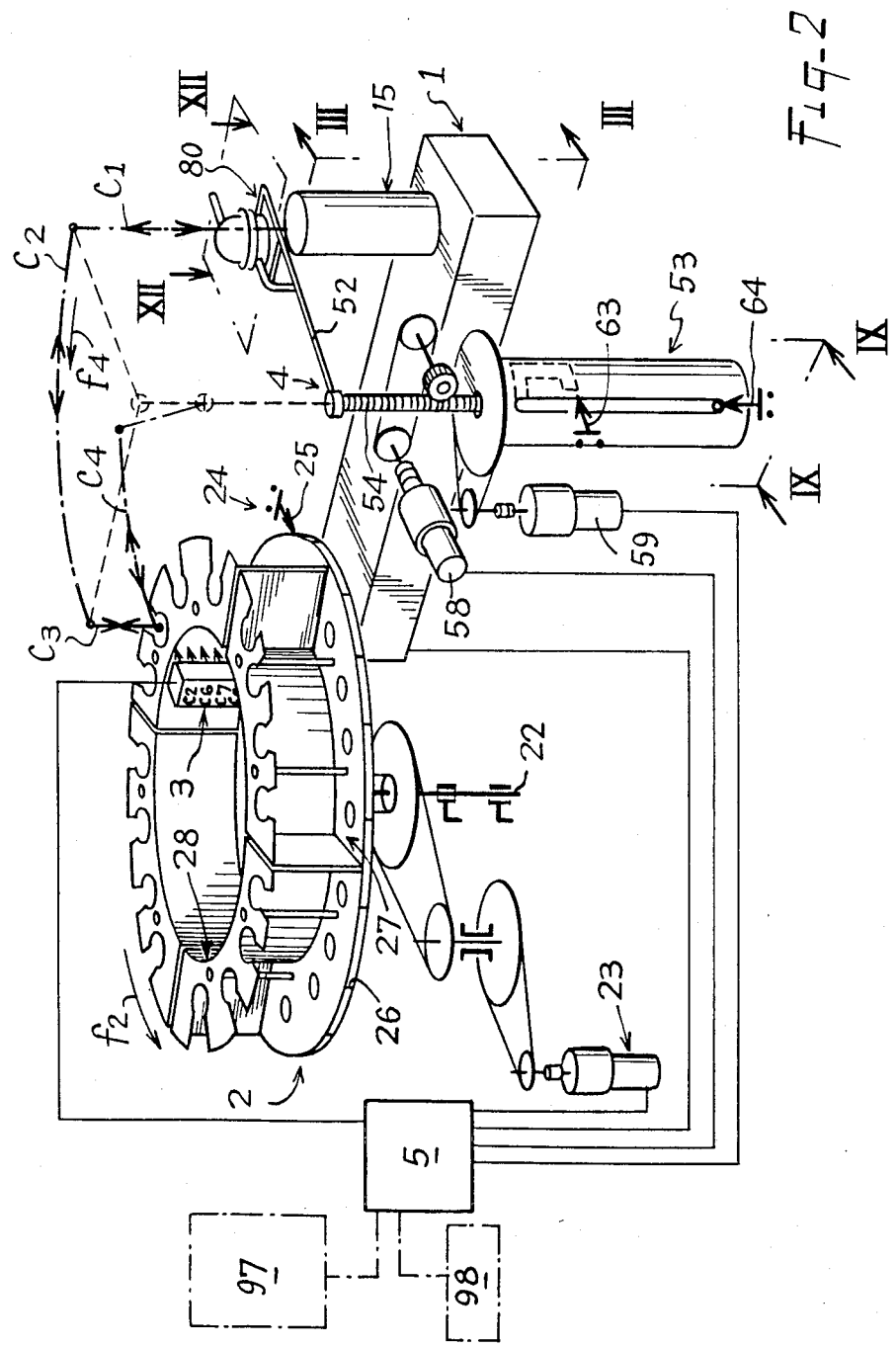
FIG. 2 is an exploded schematic view of the principal elements constituting the apparatus.

Referring now to the drawings, FIGS. 1 and 2 show that the mineralization apparatus according to the invention is principally constituted by a micro-wave heating unit 1, by a device 2 for transporting to a fixed station, samples to be treated, by means 3 for detecting at least one characteristic specific to each sample, by a means 4 for transfer between the device 2 and the micro-wave heating unit 1, and by a control unit 5.

The above different technical means may be constructed in the form of independent modules, connectable as far as their interfunctional relations are concerned, or may be fitted, mounted, borne or fixed on a common chassis such as that designated by reference 6 in FIG. 1.

Figure 3:
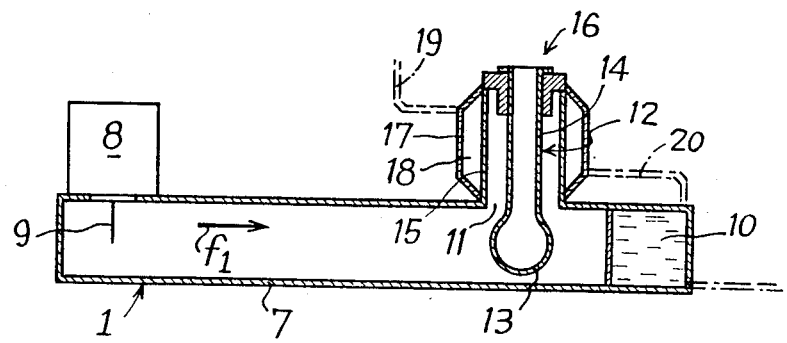
FIG. 3 is a longitudinal section taken along plane III—III of FIG. 2, without the device defining the cavity of application.

The micro-wave unit 1, as illustrated in FIG. 3, comprises micro-wave heating chamber 7 associated with a generator 8 of which the antenna 9 is placed to emit into the chamber 7 micro-waves moving in a general direction $f_1$.

In its terminal part opposite antenna 9, the chamber 7 comprises a water trap chamber 10 constituting a chamber for absorption of the micro-waves which are not absorbed in the course of the treatment.

Between the antenna 9 and the water trap chamber 10, the chamber presents, in its upper wall, opening 11. The section of passage of the opening 11 corresponds, to within the clearance, to the largest transverse horizontal section of container 12 adapted to contain a sample of the compound to be treated. The shape of container 12 is adapted to the nature of the sample and to the treatment to which it is to be subjected. For example, container 12 is a recipient of the flask type made in particular of glass and comprising portion 13 for retention, capable of being placed inside the chamber 7. The sample container portion 13 is extended by a neck 14 of considerable length projecting out of the chamber 7 through opening 11. The sample containing portion may be generally semi-spherical in form or have a flat bottom if the container is of the ordinary tubular type or in the form of a bulb in the case of a flask.

Furthermore, the chamber 7 comprises a stack 15 bordering the opening 11 and rising vertically over a height which is substantially less than the length of the neck 14. The height of the stack is also determined as a function of the section of the opening 11 and of the frequency of the micro-waves in order to constitute an absorption member opposing the emission of micro-waves outside the chamber 7. The container 12 is associated with an end piece 16 surrounding the top end of the neck 14 in order to perform a function of suspension and a function of grip/transport and centering of the container 12.

The stack 15 is associated with a peripheral envelope 17 with which it defines an annular volume 18 which is placed in relation with a circuit 19 for the circulation of a fluid regulating the temperature imposed on the neck 14 by the heating of the compound subjected to the micro-wave radiation inside the chamber 7. According to a preferred embodiment of the invention, the circuit 19 presents an intercommunication 20 between the capacity 18 and the water-trap chamber 10.

The device 2 is designed to perform a function of feeding, in random succession and of individual presentation to a fixed station, containers 12 each containing a sample of a product having to be subjected to mineralization.

To perform this function, the device 2 may be made in several different ways. For example, it may be constituted by an endless conveyor or the like comprising housings for receiving and supporting individual containers. Such a conveyor moves in front of a container loading station, in front of a fixed presentation station and in front of a station for unloading the containers in which the product has undergone the mineralization treatment. Loading station is understood to mean a reception unit located within the limits of several lines supplying containers containing compounds coming from different sources or separate stations of an installation for carrying out a process for preparing, obtaining or manufacturing products. Depending on the specific character of the compounds to be treated, the role of such a work unit is to add the or each dose of acid necessary for carrying out mineralization by wet process. Such a unit is not directly part of the object of the invention and may be designed and organized in several different ways to respond to the object which is that of supplying the device 2 with containers containing samples of one or more products to be treated associated with their basic reagents.

As illustrated in FIGS. 1, 2 and 4 to 7, the device 2 may also be made in the form of a carrousel or a barrel rotating on a vertical axis.

In such a case, the device 2 comprises a plate 21 borne by a vertical shaft 22 adapted to be driven in rotation, for example in the direction of arrow $f_2$, by a electric gear motor unit 23. Supply of unit 23 is controlled by the control unit 5 and by a stationary indexing means 24. According to one arrangement of the invention, the stationary indexing means 24 comprises a position detector 25, for example an electro-mechanical contactor placed to cooperate with marks 26 made on the outer periphery of the plate 21.

The carrousel defines on its periphery and in register with marks 26, housings 27 for receiving and supporting individual sample containers. Such housings may result from multiple structural configurations of the plate 21, to take into account the necessary facility of support, immobilization, but also of positioning and extraction of each container.

According to a seemingly advantageous constructive arrangement, the housings 27 are defined by removable baskets 28 in the form of segments of ring for example, each of an angular span substantially equal to 90°.

Figure 4:
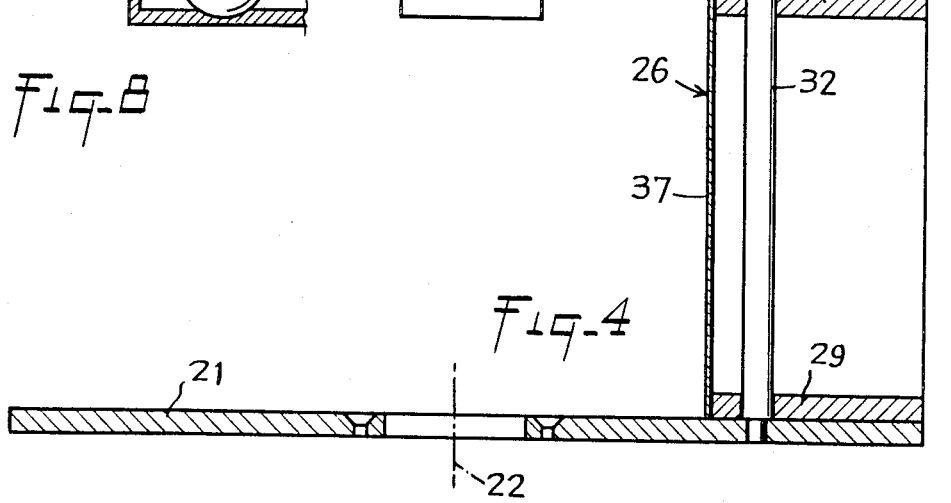
FIG. 4 is a partial sectional elevation of one of the elements constituting the object of the invention.
Figure 5:
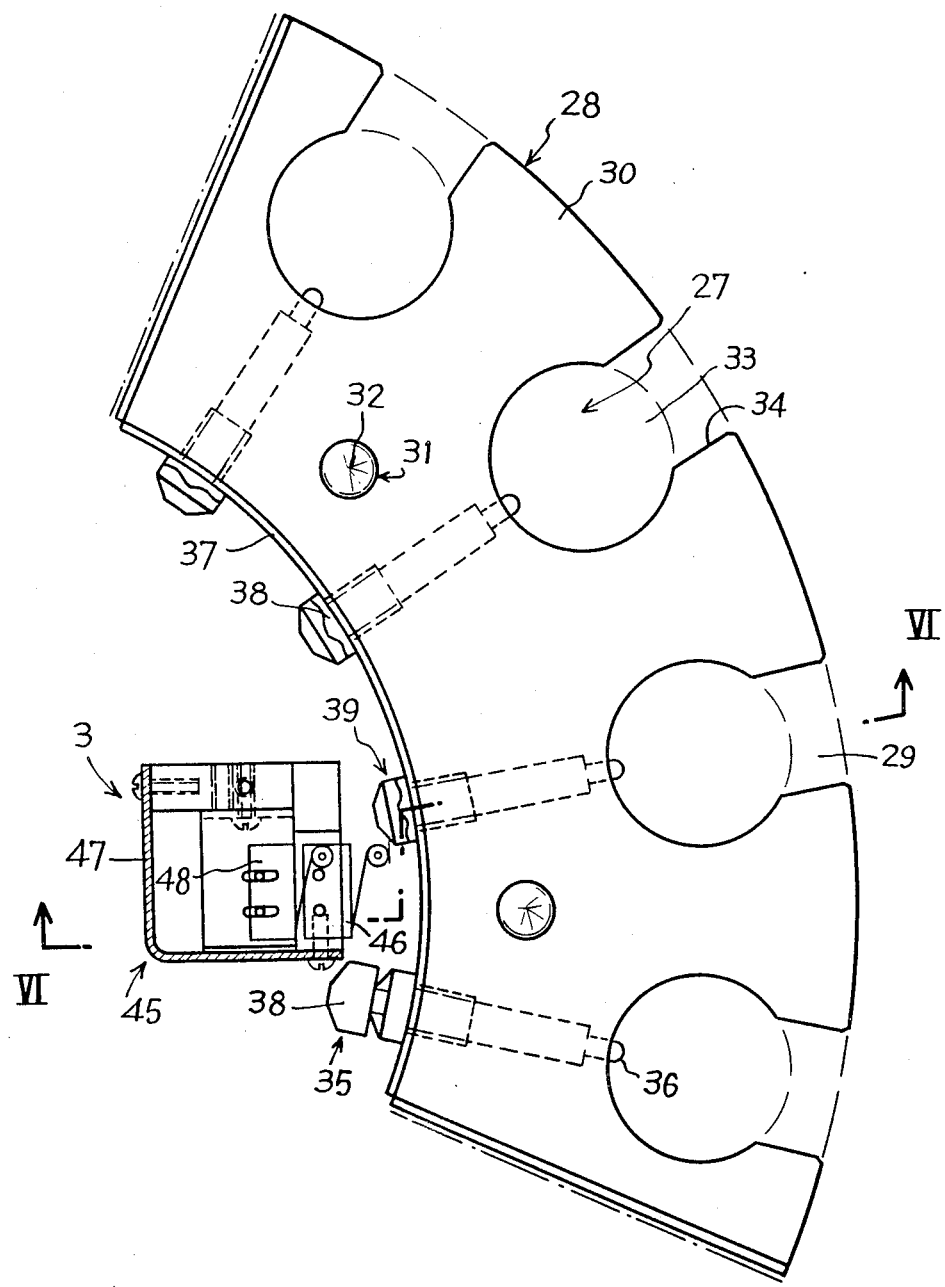
FIG. 5 is a plan view taken along line V—V of FIG. 4.
Figure 6:
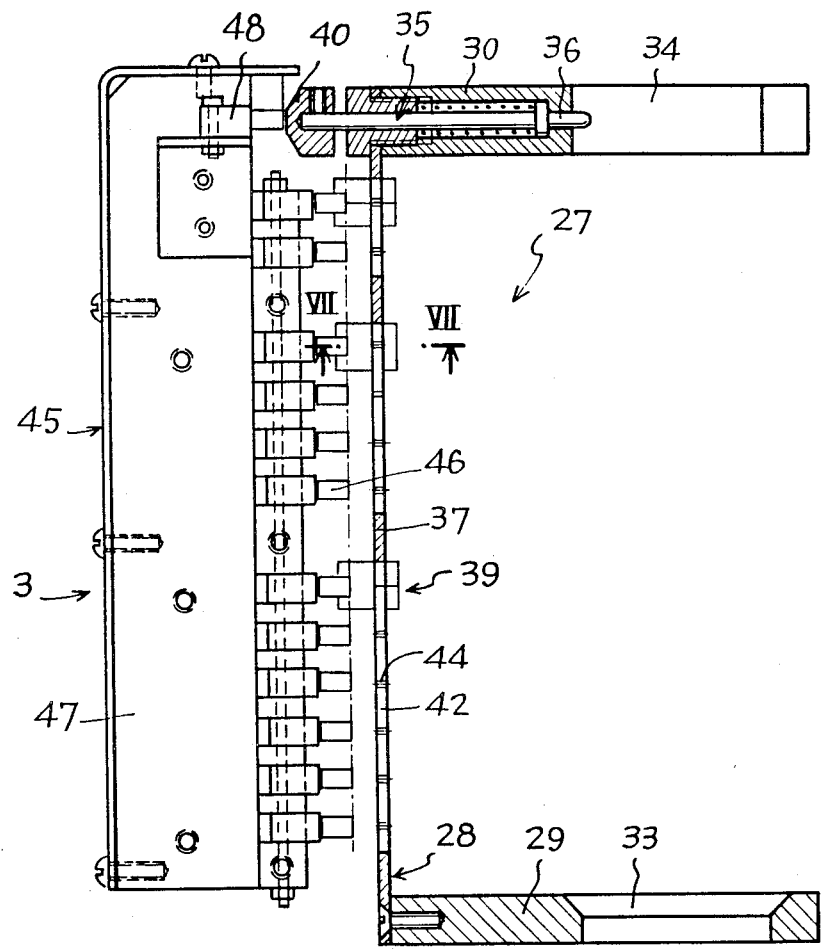
FIG. 6 is a sectional elevation taken along line VI—VI of FIG. 5.

FIGS. 4 to 6 show in greater detail the shape of each basket 28 constituted substantially in the form of a box open on its outer periphery. Such a box comprises, in its parallel horizontal walls 29 and 30, holes 31 enabling such a basket to be fitted vertically on pins 32 rising from the plate 21. This makes it possible to fit rapidly and to extract, in the same manner, any one of the baskets 28 with respect to the device 2.

Each basket 28 defines a certain number of housings 27, for example four in number, each materialized by a recess 33 made in the wall 29 in order to constitute a seat for receiving the bulb 13 of a container 12. Each housing is also materialized by an oblong slot 34 open from the outer periphery and made in the upper wall 30 for engagement of the neck 14 equipped with the end piece 16.

By these means, a container may be supported and immobilized vertically in a housing 27 and an operator in charge of operating the apparatus can ensure supply of device 2 by preparing baskets 28 from a loading unit of the type such as the one evoked hereinabove.

Each housing 27 comprises a presence detector 35 connected to the control unit 5 for monitoring, in cooperation with the latter and the stationary indexing means 24, supply of the motor 23 which may for example be of the step-by-step type.

The presence detector 35 is, for example, constituted by a physical sensor 36 borne by one of the walls constituting the basket, so as to be influenced by the presence of a container in the housing 27 to which it is allocated. The sensor 36 is, for example, of the elastic return type and comprises, outside the back wall 37 of the basket 28, a catch 38 whose function will be apparent hereinafter.

It is obvious that other types of presence detectors may be employed for bringing, in some manner or another, to the control unit 5, the logical information as to the presence or absence of a container 12 in a housing 27.

Means 3 (FIGS. 5 to 7) may be of different design, their function always being to bring to the control unit 5 the information corresponding for example to the type of treatment to be carried out, to the temperature having to be imposed on the sample and to the duration of treatment to be imposed on such a sample.

With a view to performing these functions, means 3 may for example employ mobile catches 39 specific to each housing 27 and each adapted to occupy a determined adjustable position along a vertical guide.

Figure 7:
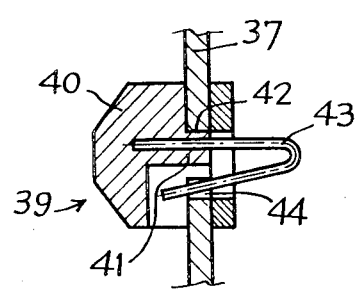
FIG. 7 is a partial sectional elevation taken, on a larger scale, along line VII—VII of FIG. 6.

By way of example, the catches 39, three in number, may each be made in the form of a piece 40 comprising, as illustrated in FIG. 7, a shank 41 engaged and guided in a slot 42 presented vertically by the back 37 of each basket. Each piece 40 is associated with an elastic pin 43 for immobilizing the catch 39 in any one of several positions predetermined by complementary notches 44 made in one of the parallel edges of the slot 42.

In this way, when a basket 28 is loaded, the operator places the catches 39 as a function of a coded position corresponding to a type of treatment, to a temperature and to a duration of treatment specific to each sample disposed in the basket.

Means 3 further comprise a bank 45 of contactors 46 which are borne by a rack 47 rising vertically, from the means for supporting the device 2. In the present case, the contactors 46 are placed inside the barrel or carrousel, substantially parallel to the inner periphery defined by the successive backs 37 of the different baskets 28. The different contactors 46 are organized into groups corresponding to the functions having to be assumed, such as those of definition of the treatment, of the temperature and of the duration. The different contactors 46 are electrically connected to the control unit 5 whose role is to ensure cyclic and sequential operation of the apparatus, in automatic manner.

The rack 47 is fixed adjustably so that the different contactors 46 occupy positions corresponding to all the states of adjustment likely to be conferred to the catches 39 by the notches 44.

FIG. 6 also shows that the rack 47 comprises a supplementary contactor 48 which is reserved for cooperation with the catch 38 of the detector 35, when the latter is constituted in the form of a physical presence detector. The contactor 48 is also connected to the control unit 5.

Means 3 described hereinabove are not limiting and equivalent technological arrangements may be retained for performing the same function.

Figure 8:
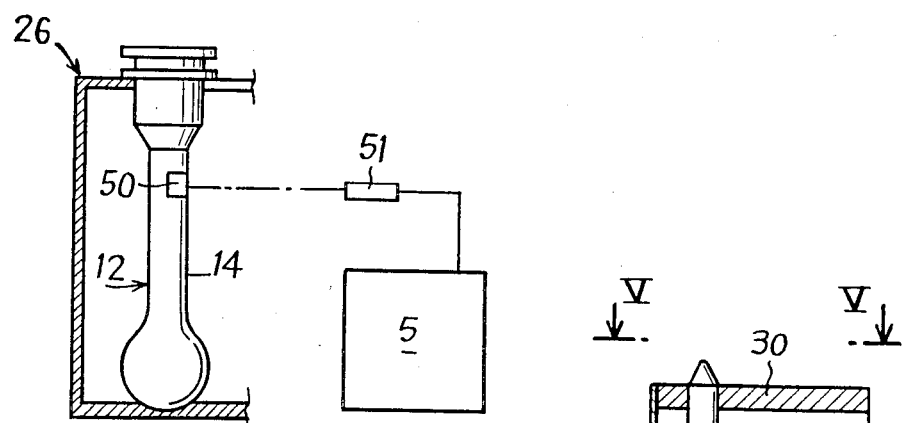
FIG. 8 is a schematic view illustrating a development of one of the elements constituting the object of the invention.

For example, FIG. 8 shows a variant embodiment consisting of providing the neck 14 of each container 12 with a frame or an area 50 of which the surface state is adapted to receive deletable coded information which may be brought by any suitable means. Means 3 comprise, in that case, a reader 51, for example of optical type, also connected to the control unit 5.

The transfer station 4 comprises an arm 52 whose role is to ensure taking over and transfer of a sample container between the fixed station 14 and the stack 15 and vice versa, as shown schematically in FIG. 2.

To this end, the transfer means 4 comprises an assembly 53 for motorization of the arm 52. The assembly 53, illustrated in greater detail in FIGS. 9 to 11, comprises a shaft 54, of generally vertical direction, of which the upper terminal part supports the arm 52. The shaft 54 is mounted freely to rotate and slide axially by smooth bearings 55 in a cylinder 56 fixed on a support plate 57, for example fitted on the chassis 6.

The shaft 54 is associated with two drive members 58 and 59, for causing it to describe a reciprocating rectilinear axial displacement and a reciprocating partial angular displacement, respectively.

Drive member 58 is constituted by an electric motor 60 borne by the cylinder 56 and driving a toothed gear 61 permanently meshing with a cylindrical rack 62 presented by shaft 54 over a part of its length. End-of-stroke contactors 63 and 64, such as those shown schematically in FIG. 2, are provided to determine the end positions of reciprocating axial displacement of the shaft 54. Actuation of contactors 63 and 64 is ensured by a finger 65 borne by the lower terminal part of the shaft 54.

Drive member 59 comprises an electric motor 66 controlling, by a gear 67, the direct or indirect rotation of a sleeve 68 mounted to rotate but immobilized axially on the cylinder 56 by smooth bearings 69. The sleeve 68 concentrically surrounds part of the cylinder 56 and presents an axial slot 70 through which is permanently engaged the finger 65 of the shaft 54. The finger 65 also passes through a slot 71 made axially on that part of the cylinder 56 surrounded by the sleeve 68. The slot 71 communicates, in its upper part, with a slot 72 made peripherally over an angular value corresponding to the range of pivoting having to be imposed on the arm 52. The peripheral slot 72 communicates with an axial slot 73 of shorter length than slot 71 and which terminates in a peripheral slot 74 extending in return parallel to slot 72 but over an angular range smaller than the latter.

The linear and angular measurements of slots 71 to 74 are characteristic of the movements having to be imposed on arm 52 and are made in order to present dimensions in relation with these movements.

Angular end-of-stroke contactors along slots 72 and 74 are provided to cooperate with finger 65.

Supply of electric motors 60 and 66 is controlled by the control unit 5 and by detectors detecting the extreme position of rectilinear or angular stroke of arm 52, said detectors being connected to the control unit 5.

Figure 12:
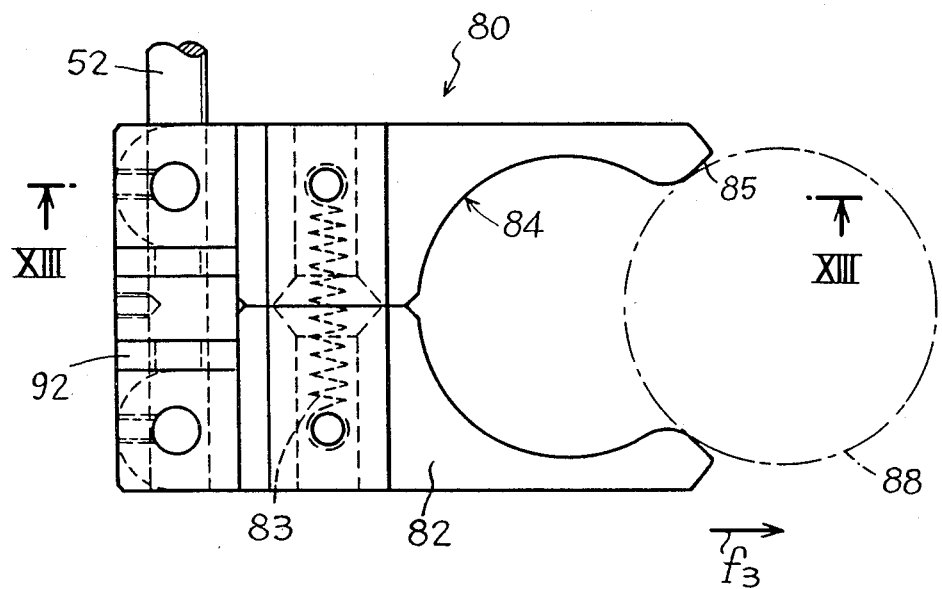
FIG. 12 is a plan view taken, on a larger scale, along line XII—XII of FIG. 2.
Figure 13:
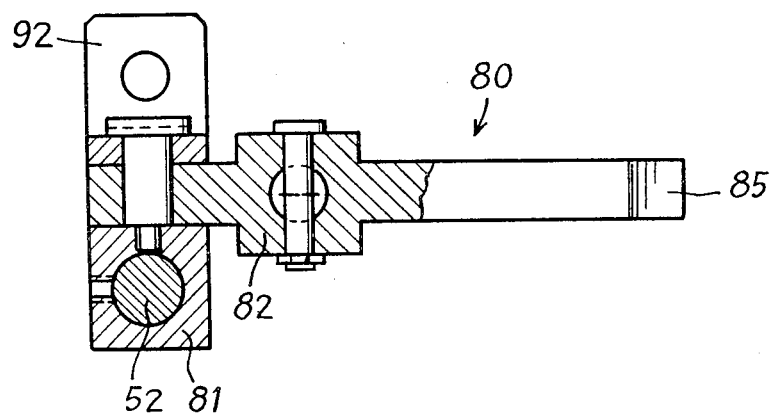
FIG. 13 is a section taken along line XIII—XIII of FIG. 12.

With a view to performing the function of transfer, the arm 52 is associated, by its end opposite that borne by shaft 54, to a gripping member 80, such as shown in greater detail in FIGS. 12 and 13. The gripper member 80 comprises a body 81 adapted to be fitted on the arm 52 by means for adjustment in axial position. The body 81 supports two articulated jaws 82 opposite each other and which are urged into permanent relative closure by an elastic member 83, for example of the helical draw spring type.

The jaws 82 are made to define, by their opposite edges, a gripping section 84 complementary of the end piece 16 described with reference to FIG. 3. In addition, the free terminal parts of the jaws 82 comprise, on the inner edges, inclined ramps 85 together defining a passageway with convergent edges for the introduction of the end piece 16. Ramps 85 make it possible to obtain automatic opening of the jaws 82, against the action of the spring 83, as soon as they come into contact with the end piece 16 against which they are pressed in the direction of arrow $f_3$.

Figure 14:
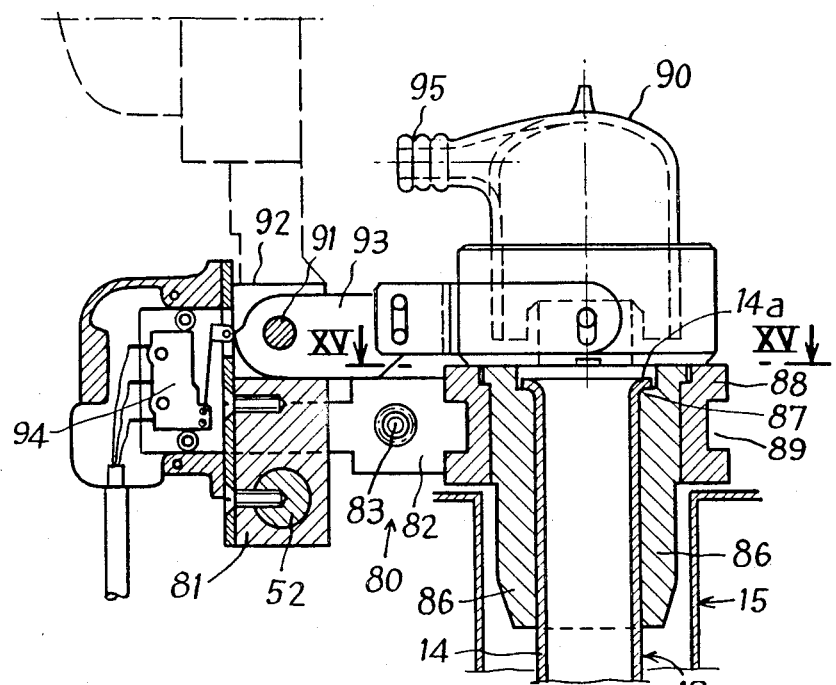
FIG. 14 is a sectional elevation illustrating another element constituting the invention.
Figure 15:
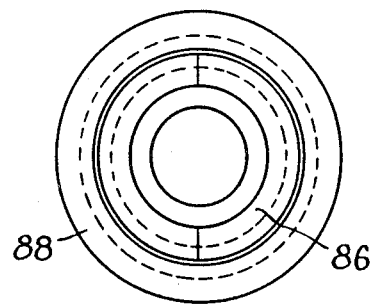
FIG. 15 is a plan view taken substantially along line XV—XV of FIG. 14.

The shape of jaws 82 is chosen to be complementary to the constitution of the end piece 16 which comprises (FIGS. 14 and 15), two half-shells 86 adapted to be fitted by radial application about the neck 14 of a container of which the upper edge 14a is placed in abutment against a shoulder 87 defined by the inner periphery of the half-shells 86. Holding of the half-shells 86 is ensured by a ring 88 adapted to be threaded on the half-shells 86 to bear, in axial abutment, on these latter in the direction of the action of gravity. The ring 88 is provided with a peripheral groove 89 of which the diameter corresponds, to within the clearance, to the gripping section 84 defined by the opposite faces of the jaws 82 in closed position.

The gripping member 80 is completed by a cover 90 mounted to pivot, in rocking manner, by a horizontal pin 91 on a stirrup 92 rising up from the gripper body 81. The articulated assembly of cover 90 is, for example, ensured by a lever 93 cooperating with at least one contactor 94 assessing either the closed position of the cover 90 in abutment on the upper edge of the ring 88, as illustrated in solid lines in FIG. 14, or the raised position, as shown in broken lines. Contactor 94 is connected to control unit 5.

The cover 90 comprises a tube 95 in permanent relation, as shown in FIG. 1, with a supple pipe 96 leading to a pumping and suction unit (not shown).

The control unit 5 is preferably constituted or programmed to establish, by taking into account the information supplied by the different contactors or detectors, an entirely automatic operation of the apparatus by controlling the succession of the different sequences of the same cycle of treatment and by defining the operational parameters of the phase of treatment proper, and this for each cycle of operation, i.e. in manner specific to each sample.

However, it must be considered that the unit 5 may also be connected to a module 97 for displaying the characteristic information taken by the means 3. The unit 5 may, in that case, be provided with a control panel 98 making it possible manually to display the characteristic information in order to trigger off automatic operation of the different sequences of one given cycle, by opposition to the previous case where the succession of each different cycle is taken over automatically by the control unit 5.

Similarly the phases of treatment may be triggered off by the position of the container, in relation with instructions of treatment introduced into a programme of automatic operation.

The apparatus described hereinabove operates in the following manner.

From the position illustrated in FIG. 2, it may be considered that the apparatus is in a state of end of a cycle of treatment of a sample disposed in a sample container placed in the chamber 7 of the micro-wave heating unit 1, borne by the gripper member 80. In such a state, operation of the micro-wave oven is interrupted.

Unit 5 then controls supply of the motor 60, so as to provoke elevation of the shaft 54 over a vertical stroke corresponding to the necessary measurement for extracting the bulb 13 from the stack 15. This vertical rectilinear stroke is designated by reference $C_1$ in FIG. 2.

An examination of FIGS. 9 to 11 will show that this phase of operation of the motorization assembly 53 may develop without incidence between the different means constituting this assembly, since the finger 65 is then displaced axially in the slots 70 and 71.

Via the end-of-stroke contactor, such as 63, the unit 5 then controls the stoppage of supply of the motor 60, then the supply of motor 66 for controlling by the sleeve 68 and the finger 65 the annular displacement of the arm 52 in the direction of arrow f. This angular stroke of the arm 52 is determined to displace the sample container 12 from being plumb with the stack 15 to being plumb with the housing 27 from which it was previously extracted. This stroke of angular displacement is designated by reference $C_2$ in FIG. 2.

When the end-of-stroke contactor provided to this end determines the end of stroke $C_2$ in the direction of arrow $f_4$, the unit 5 interrupts supply of the motor 66 and controls that of motor 60, so as to provoke rotation of the latter inverse to that of the phase described previously.

The shaft 54 is thus urged into descending vertical rectilinear displacement over the whole length of the slot 73, this corresponding to the deposit of the container 12 in the housing that it occupied with stabilization, by abutment of the bulb 13 in the recess 33 and, simultaneously, abutment of the lower edge of the ring 88 on the top of the wall 30 of the corresponding basket 26.

This descending stroke, designated by reference $C_3$ in FIG. 2, is determined by an end-of-stroke contactor making it possible to control, by unit 5, stoppage of the supply of motor 60 and supply of motor 66 in order to provoke a rotation of the latter inverse to that previously described.

This makes it possible to cause the finger 65 to pass through the slot 74 and corresponds to a stroke of the arm 52 designated by reference $C_4$ in FIG. 2. An examination of this Figure shows that the gripper member 80 is then extracted from the end piece 16 and displaced angularly up to a stand-by position, whilst being disengaged from device 2.

This stand-by position, determined by an end-of-stroke contactor, allows the unit 5 to control the supply of the gear motor group 23, so as to cause the shaft 22 to rotate in the direction of arrow $f_2$. The plate 21 is displaced angularly by the value of the pitch corresponding to the bringing into cooperation of a mark 26 with the stationary indexing means 24. The contactor 25 supplies the unit 5 with information making it possible to interrupt supply of the gear motor unit 23, insofar as the housing 27, thus presented at the fixed station 24, is considered as being occupied by a container via the corresponding presence detector 35. In the event of the presence detector 35 not furnishing information to this end, supply of the gear motor unit 23 is maintained in order to present the following housing 27 at fixed station 24.

In the present case, the information from the presence detector is ensured via the catch 38 which, upon rotation in the direction of arrow $f_2$, actuates the corresponding contactor 48.

The effect of the presentation of a housing 27 at the fixed station 24 is to control, by the different catches 39, the corresponding contactors 46 of the rack 45 and thus to furnish to the unit 5 the elements corresponding to the operational parameters having to be imposed on the micro-wave heating unit 1.

Such a presentation at the fixed station also allows unit 5 to control the motorization assembly 53 to cause the arm 52 to effect strokes $C_4$ to $C_1$, in the order inverse to what is described hereinabove. The gripper member 80 thus ensures the taking over of another container containing a sample to be treated, extracts this container in stroke $C_3$, displaces this container from being plumb with its housing 27 to being plumb with the stack 15 in stroke $C_2$, then descends the container into the cavity 7 in stroke $C_1$.

The end-of-stroke contactor 64, determining the positioning of the flask in the oven, makes it possible to trigger off, by unit 5, the operation of the latter in accordance with the parameters initially memorized, insofar as the contactor 95 ascertains the closed position of the cover 90.

The pumping and suction unit is started up in synchronized manner for the time necessary for ensuring removal of the fumes and vapours released during the initial and/or principally reactive rise in temperature of the sample subjected to the application of the microwaves delivered by the unit 1 at the power and in a time corresponding exactly to the information addresed to unit 5 by the means 3.

At the end of the treatment phase, the apparatus is again in the initial state considered by supposition, as the beginning of the cycle of operation which has just been described. Another cycle of operation may then unfold.

As follows from the foregoing, the apparatus according to the invention makes it possible to effect a treatment of mineralization prior to a treatment of analysis, proceeding automatically to apply an individual treatment specific for each sample of product to be treated, whatever the order and succession of the samples which may thus be presented, totally at random.

Such a possibility of individual, automatic treatment of samples of various natures or of the same nature, having to be subjected to different treatments, makes it possible to digest, by an appropriate apparatus, rapidly and effectively, a large number of samples and to reduce considerably the time for obtaining any information concerning change or correction of the parameters for development of the phases of a process for the treatment, manufacture or preparation of a final product.

The use of a treatment oven comprising a permanently open cavity facilitates automatic introduction and extraction of a container through the stack 15 forming an obturator with respect to the microwaves. The structure of the stack also enables the conditions of circulation of the fluid for regulating the temperature of the neck 14 of the flask to be varied. It thus becomes possible to facilitate maintenance of this neck at a temperature appropriate for the formation of a phase of condensation in order to avoid extraction by the vapours and fumes of particles of compounds of the product in the course of mineralization. After mineralization, this gives a solution making it possible to proceed with a particularly fine and precise, and especially reproducible, analysis of the compounds to be isolated.

If, in general, it is question of cooling the neck 14, it is sometimes necessary to raise this temperature, for example, in the case of a mineralization by wet process and with oxidizing phase to ensure elimination of the reaction products. The stack also enables this result to be attained.

Another advantage of the invention lies in the fact that the application of micro-waves to the sample makes it possible to eliminate the risks of foaming of the compound/reagent association, with the result that the apparatus may operate automatically without any risk and with minimum surveillance.

Furthermore, it should be noted that the different means according to the invention enable all risk of random operation to be eliminated, being given that the operation of the micro-wave unit, triggered off by unit 5, depends on means of assessment of the execution and correct succession of the different intermediate phases and on knowing the position of the cover 90 whose role is to remove the fumes and vapours by the pumping and suction unit.

The invention is not limited to the examples described and shown, as various modifications may be made thereto without departing from its scope.

What is claimed is:

1. A mineralization apparatus for the individual, automatic, treatment of samples comprising:
   a micro-wave generator for emitting micro-waves into a micro-wave heating chamber,
   a plurality of sample container means each having an enlarged sample containing portion at a lower end thereof and an upwardly extending neck portion connected thereto,
   a micro-wave heating chamber adapted to receive the sample containing portion of one of said plurality of sample container means said micro-wave heating chamber comprising a housing having an upper wall and defining in said upper wall an opening through which said sample containing portion of said sample container means can be placed in and removed from said chamber,
   a stack bordering said opening in said upper wall of said micro-wave heating chamber adapted to surround the upwardly extending neck portion of said sample container means when the sample containing portion is placed in said micro-wave heating chamber,
   a transport station for receiving said sample container means,
   means for randomly supplying sample container means in individual housings, in random succession and individual presentation to said transport station,
   means for detecting at least one characteristic of treatment specific to each sample transported to the transport station in sample container means,
   means at said transport station for individual transfer of sample container means between said container supply means and the micro-wave heating chamber, and
   means for controlling the automatic operation of the apparatus in a cycle specific to each sample based upon the at least one characteristic of treatment specific to each sample detected.

2. The apparatus of claim 1, wherein said detection means comprises:
   a marking surface located on said upwardly extending neck portion of the sample container means,
   deletable, coded information contained on said marking surface, and
   means for reading the coded information.

3. The apparatus of claim 1, wherein said detection means comprises:
   mobile catches which are adjustable in position, and
   contactors connected to the control means and borne by a fixed supporting rack so as to be positioned on the possible geometrical loci of displacement of the catches.

4. The apparatus of claim 1, wherein said control means comprises:
   means for displaying the results detected by said detection means, and
   a manual control panel for displaying the results as operational parameters of the micro-wave heating chamber.

5. The apparatus of claim 1, wherein said random supply means comprises a drive motor member controlled by a control unit, means for detecting the presence of sample container means and means for indexing said individual housing on said supply means.

6. The apparatus of claim 5, wherein said random supply means comprises an endless conveyor advancing in front of a station for loading sample container means and a station for unloading sample container means respectively upstream and downstream of said transfer means.

7. The apparatus of claim 5, wherein said random supply means comprises a carousel or rotating barrel having removable baskets for supporting sample container means.

8. The apparatus of claim 1, wherein said stack is bordered by a concentric envelope defining an annular volume connected to a circuit for circulation of a fluid to regulate the temperature of the neck portion of the sample container means.

9. The apparatus of claim 8, wherein said micro-wave heating chamber includes a water-trap chamber which communicates with the annular volume surrounding said stack.

10. The apparatus of claim 1, wherein said transfer means comprises:
    a gripping member,
    an arm for supporting the gripping member,
    means, controlled by said control means, for moving said arm in reciprocating horizontal angular displacement between two extreme positions corresponding to being plumb with the fixed station and with the opening in the upper wall of the micro-wave heating chamber and in reciprocating vertical rectilinear displacement in each of the end positions, and
    means for detecting the different positions of the arm, connected to said control means.

11. The apparatus of claim 10, wherein said means for moving said arm comprises:

a vertical shaft bearing the arm of the gripping member, a drive member urging the shaft in reciprocating partial angular rotation on its axes.

12. The apparatus of claim 10, wherein the gripper member comprises two jaws urged towards closure by an elastic member and defining in a closed position an open section capable of tightening around the neck portion of a sample container means and by their ends a passageway with convergent edges for engagement of a neck portion of a sample container means.

13. The apparatus of claim 10 or 12, wherein the gripper member comprises two jaws which define in closed position an open section for holding the neck portion of a sample container means.

14. The apparatus of claim 13, wherein the gripper member comprises:
two semi-cylindrical half-shells adapted to surround the neck portion of a sample container means and to cooperate in axial abutment with the end edge of said neck portion, and
a ring surrounding the half-shells, cooperating in axial abutment with the half-shells and having in its outer peripheries an annular groove for the engagement of the jaws of the gripper member.

15. The apparatus of claim 10 or 12, wherein the gripper member comprises a body forming a stirrup on which is disposed a rocking cover associated with a position detector connected to the control unit, said cover comprising a tube connected to a pumping and suction unit.

* * * * *